United States Patent
Moon et al.

[11] Patent Number: 6,162,826
[45] Date of Patent: Dec. 19, 2000

[54] GENIPIN DERIVATIVE HAVING ANTI HEPATITIS B VIRUS ACTIVITY

[75] Inventors: Sung Hwan Moon; Hea Jin Choi; Su Jin Lee; Jea Uk Chung; Jai Hyun Kim; Dong Hoon Chung; Moon Soo Park; In Koo Cho; Kun Hyock Choi, all of Kyunggi-do, Rep. of Korea

[73] Assignee: Choongwae Pharmaceutical Corporation, Seoul, Rep. of Korea

[21] Appl. No.: 09/284,540

[22] PCT Filed: Oct. 8, 1997

[86] PCT No.: PCT/KR97/00188

§ 371 Date: Apr. 14, 1999

§ 102(e) Date: Apr. 14, 1999

[87] PCT Pub. No.: WO98/17663

PCT Pub. Date: Apr. 30, 1998

[30] Foreign Application Priority Data

Oct. 18, 1996 [KR] Rep. of Korea ............ 96-46732

[51] Int. Cl.[7] .................. A61K 31/352; C07D 311/94
[52] U.S. Cl. ............................. 514/456; 549/396
[58] Field of Search ................ 549/396; 514/456

[56] References Cited

U.S. PATENT DOCUMENTS 5,459,160  10/1995  Fujii et al. ..................... 514/460

FOREIGN PATENT DOCUMENTS 43 23 567 A1  1/1994  Germany .
WO 92/06061  4/1992  WIPO .

OTHER PUBLICATIONS

Wysokinska et al., Chem. Abstract 117:23243, 1992.
Nakane et al., Chem. Abstract 93:186574, 1980.
Chemical Abstracts, vol. 111, 1989, p. 417 Abstract No. 239518.

*Primary Examiner*—Mukund J. Shah
*Assistant Examiner*—Deepak R. Rao
*Attorney, Agent, or Firm*—Peter F. Corless; Christine C. O'Day; Edwards & Angell, LLP

[57] ABSTRACT

The present invention relates to a novel genipin derivative represented by formula (I), which has anti hepatitis B virus (HBV) activity, in which $R_1$ represents lower alkyl, benzyl, etc., $R_2$ represents hydroxymethyl, formyl, acetyl, etc., $R_3$ represents methoxycarbonyl, formyl, etc., its pharmaceutically acceptable salt, and stereoisomer.

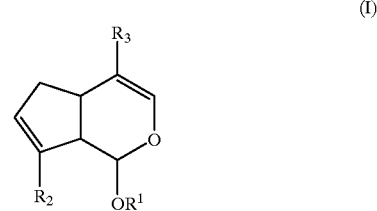

(I)

5 Claims, No Drawings

GENIPIN DERIVATIVE HAVING ANTI HEPATITIS B VIRUS ACTIVITY

This is a national stage application of International Application No. PCT/KR97/00188, filed Oct. 8, 1997.

TECHNICAL FIELD

The present invention relates to a novel genipin derivative represented by the following formula (1), which has an anti hepatitis B virus (HBV) activity:

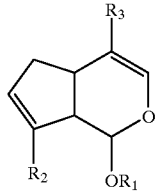

(I)

in which $R_1$ represents lower alkyl, benzyl, or $C_1$–$C_{12}$ alkanoyl which can be substituted with phenyl, phenoxy, pyridyl, t-butyl or thienyl, $R_2$ represents hydroxymethyl, formyl, acetyl, hydroxyiminomethyl, methoxyiminomethyl, lower alkylaminomethyl, acetylthiomethyl, mercaptomethyl, 2,2-dimethyl-1,3-dioxolan-5-ylmethyloxymethyl, 2,3-dihydroxypropyloxymethyl, 6-aminofuran-9-ylmethyl, 4-amino-2-hydroxy-5-methylpyrinmidin-1-ylmethyl, 2,4-dihydroxy-5-methylpyrimidin-1-ylmethyl, 5-hydroxymethyl-1,3-oxathiolan-2-yl, or $C_1$–$C_{12}$ alkanoyloxymethyl which can be substituted with phenyl, phenoxy, pyridyl, t-butyl or thienyl, and $R_3$ represents methoxycarbonyl, formyl, hydroxyiminomethyl, methoxyiminomethyl, 4-methoxybenzyloxymethyl or acetyloxymethyl, provided that $R_3$ is not methoxycarbonyl when $R_1$ is lower alkyl and $R_2$ is hydroxymethyl, formyl or hydroxyirinomethyl, its pharmaceutically acceptable salt, or stereoisomer.

The present invention also relates to a pharmaceutical composition comprising as an active ingredient the compound of formula (I), which can be effectively used for the treatment of hepatitis B.

BACKGROUND ART

It has been reported that the known iridoids genipin represented by the following formula (II) and aucubin represented by the following formula (III) are natural substances, and act as a therapeutic agent for hepatitis B through the mechanism to inhibit the HBV replication (see, Korean Patent Laid-open No. 94-1886).

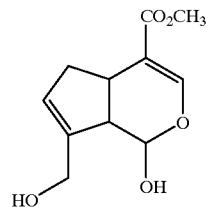

(II)

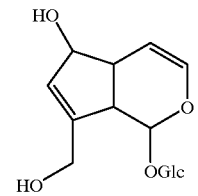

(III)

Said genipin of formula (II) and aucubin of formula (III) have some in vivo activities such as liver-protection, inhibition of biosynthesis of RNA and protein, detoxification as well as antiviral activity. Particularly, it has been disclosed that genipin is also effective as an anti-tumor agent (see, Japanese Patent Laid-open No 80/164625). However, these compounds may be decomposed to dialdehydes in vivo and the dialdehydes thus produced may combine with amino acid residues of proteins such as albumin. Such a series of reactions may induce some color change of urine, faces, and various internal organs into blue as well as immunotoxicities.

Compounds having a similar structure to the compound according to the present invention include the compound represented by the following formula (IV) in addition to genipin and aucubin(see, WO 92/06061 and European Patent Laid-open No. EP-0505572):

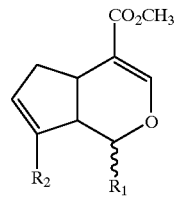

(IV)

in which $R_1$ represents benzoyloxy, hydroxy, acetoxy or ethoxyethoxy, and $R_2$ represents benzoyloxymethyl, methoxymethyl, t-butyldimethylsilyloxymethyl, carboxy or hydroxymethyl.

It is described in the above literatures that the compound of formula (IV) above may be used effectively as a therapeutic agent for hyperlipemia or as a cholagogues.

On the other hand, the present inventors have synthesized a series of novel aucubin and genipin derivatives on the basis of the prior arts as mentioned above in order to develop compounds having a superior activity to the earlier compounds on inhibition against HBV. After the antiviral activity and little cytotoxicity of the novel compounds prepared were identified, the present inventors have filed a patent application on the novel compounds (see, Korean Patent Appln. No. 95-38181).

DISCLOSURE OF INVENTION

The present inventors have continuously and intensively studied to develop novel compounds having more improved properties, and as a result, have succeeded to synthesize the new compound of formula (I) according to the present invention. By determining the antiviral activity and cytotoxicity of the compound, we have identified that the compound according to the present invention is so stable in vivo that it does not induce any side effects such as change to blue color, etc. and that it may be effectively used for the treatment of hepatitis B since it has an excellent inhibitory activity against HBV with little cytotoxicity.

Therefore, it is an object of the present invention to provide a novel genipin derivative represented by the following formula (I) which has an excellent anti HBV activity as well as little cytotoxicity:

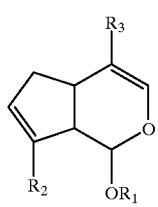

(I)

in which
- $R_1$ represents lower alkyl, benzyl, or $C_1$–$C_{12}$ alkanoyl which can be substituted with phenyl, phenoxy, pyridyl, t-butyl or thienyl,
- $R_2$ represents hydroxymethyl, formyl, acetyl, hydroxyiminomethyl, methoxyiminomethyl, lower alkylaminomethyl, acetyithiomethyl, mercaptomethyl, 2,2-dimethyl-1,3-dioxolan-5-ylmethyloxymethyl, 2,3-dihydroxypropyloxymethyl, 6-aminofuran-9-ylmethyl, 4-amino-2-hydroxy-5-methylpyrimidin-1-ylmethyl, 2,4-dihydroxy-5-methylpyrimidin-1-ylmethyl, 5-hydroxymethyl-1,3-oxathiolan-2-yl, or $C_1$–$C_{12}$ alkanoyloxyrnethyl which can be substituted with phenyl, phenoxy, pyridyl, t-butyl or thienyl, and
- $R_3$ represents methoxycarbonyl, formyl, hydroxyiminomethyl, methoxyiminornethyl, 4-methoxybenzyloxymethyl or acetyloxymethyl, provided that $R_3$ is not methoxycarbonyl when $R_1$ is lower alkyl and $R_2$ is hydroxymethyl, formyl or hydroxyirninomethyl, its pharmaceutically acceptable salt, or stereoisomer.

It is another object of the present invention to provide a pharmaceutical composition for the treatment of hepatitis B comprising as an active ingredient the compound of formula (I), as defined above, together with a pharmaceutically acceptable inert carrier.

BEST MODE FOR CARRYING OUT THE INVENTION

Among the compounds of formula (I) having a potent anti HBV activity, the preferred compounds include those wherein $R_1$ represents lower alkyl, benzyl, or $C_1$–$C_{12}$ alkanoyl which can be substituted with phenyl, phenoxy, pyridyl, t-butyl or thienyl, $R_2$ represents formyl, hydroxyiminomethyl, or $C_1$–$C_{12}$ alkanoyloxymethyl which can be substituted with phenyl, phenoxy, pyridyl, t-butyl or thienyl, and $R_3$ represents methoxycarbonyl, formyl, or 4-methoxybenzyloxymethyl.

Particularly preferred compounds of formula (I) include those wherein $R_1$ represents $C_1$–$C_{12}$ alkanoyl which can be substituted with phenyl, phenoxy, pyridyl, t-butyl or thienyl, $R_2$ represents formyl or $C_1$–$C_{12}$ alkanoyloxymethyl having the same substituent with $R_1$, and $R_3$ represents methoxycarbonyl.

In the compound of formula (I), the 1-position carbon on which —$OR_1$ group is substituted is asymmetric, and thus the compound can be present in the form of R or S or a mixture of R and S. Therefore, the present invention also includes each of these stereoisomers and their mixtures.

The compound of formula (I) according to the present invention can form a pharmaceutically acceptable salt. Such salt includes a salt with pharmaceutically acceptable acids such as asparagic acid, gluconic acid, glutamic acid, hydrochloric acid, p-toluenesulfonic acid or citric acid, etc., and a salt with acids or bases which are generally known and conventionally used in the technical field of iridoid-based compounds. These pharmaceutically acceptable salts can be prepared according to a conventional conversion method.

The compound of formula (I) of the present invention can be prepared according to the methods described below. However, it should be understood that the process for preparing the compound of formula (I) is not limited to those explained below since the compound can be easily prepared by optionally combining the various methods disclosed in prior arts, and such a combination may be conventionally carried out by a person having ordinary skill in the art.

First, processes for preparing the compound of formula (I) wherein $R_3$ is methoxycarbonyl are explained.

1) As depicted in the following Reaction Scheme 1, the compound of formula (I) wherein $R_1$ is lower alkyl or benzyl, $R_2$ is formyl, and $R_3$ is methoxycarbonyl can be prepared by reacting the hydroxy group at 1-position of genipin with a lower alcohol such as methanol, ethanol, propanol, etc., or benzyl alcohol in the presence of a Lewis acid catalyst to produce lower alkoxy or benzyloxy group in step 1, then by oxidizing the hydroxymethyl group at 7-position of compounds α-i-1 and β-i-1 into formyl in the presence of an oxidizing agent in step 2.

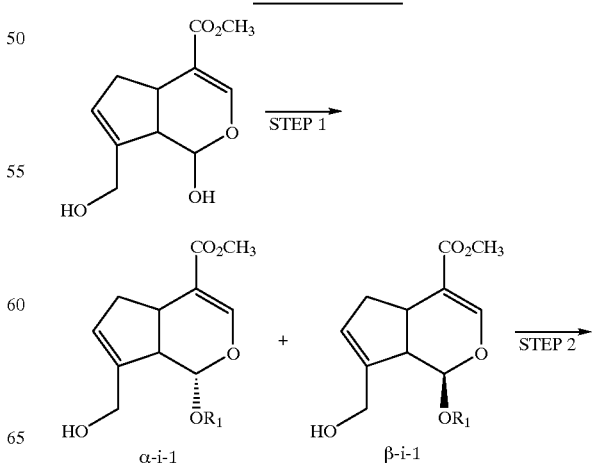

Reaction Scheme 1

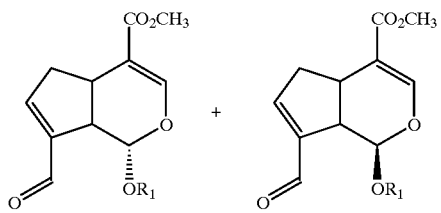

As the Lewis acid catalyst which can be used in step 1 reaction, one or more selected from a group consisting of trifluoroboron diethylether, aluminum chloride and zinc chloride can be mentioned. Since the 1-position carbon can exist in the form of S or R according to the stereochemical configuration of the $OR_1$ group, the product of step 1 reaction is obtained as a mixture of two stereoisomers each of which are designated by α-i-1 or β-i-1, respectively. The isomers can exist as separated or mixed state when they are used as a starting material in step 2 reaction. In case the step 2 reaction is carried out with the mixture, a pure isomer can be obtained through a separation process after the reaction is completed.

As the oxidizing agent which can be used in step 2 reaction, one or more selected from a group consisting of pyridiniumchlorochromate(PCC), dimethylsulfoxide-dicyclohexylcarbodiimide, dimethylsulfoxide-acetyl anhydride, dimethylsulfoxide-trifluoroacetyl anhydride, dimethylsulfoxide-oxalylchloride, dimethylsulfoxide-sulfotrioxide-pyridine, manganese(IV) oxide-(solvent such as pentane, diethylether, dimethylsulfoxide or acetonitrile) and osmium oxide can be mentioned.

2) As depicted in the following Reaction Scheme 2, each of the compounds of formula (I) wherein $R_3$ is lower alkyl or benzyl, $R_2$ is hydroxyiminomethyl, methoxyiminomethyl, 5-hydroxymethyl-1,3-oxathiolan-2-yl or lower alkylaminomethyl, and $R_3$ is methoxycarbonyl can be prepared by reacting the final product of Reaction Scheme 1 with hydroxylamine, methoxyamine, 3-mercapto-1,2-propanediol or sodiumcyanoborohydride, respectively, in the presence of a lower alkylamine. In addition, the compound of formula (I) wherein $R_1$ and $R_3$ are those as mentioned above, and $R_2$ is acetyl can be prepared by reacting the final product of Reaction Scheme 1 with methylmagnesiumiodide, then by oxidizing the product thus obtained with the same oxidizing agent used in step 2 reaction of Reaction Scheme 1.

Reaction Scheme 2

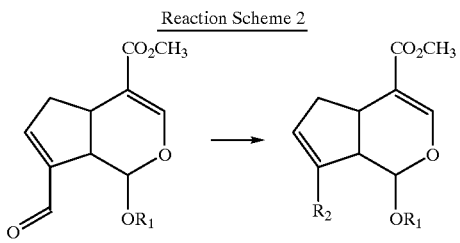

3) As depicted in the following Reaction Scheme 3, the compound of formula (I) wherein $R_1$ is lower alkyl or benzyl, $R_2$ is various alkanoyloxymethyl or acetylthiomethyl, and $R_3$ is methoxycarbonyl can be prepared by reacting the compound α-i-1 or β-i-1 in Reaction Scheme 1 with alkanoylchloride in the presence of pyridine, or with thioacetic acid in the presence of triphenylphosphine or diisopropylazodicarboxylate, respectively. Also, the compound wherein $R_2$ is mercaptomethyl can be prepared by treating the compound wherein $R_2$ is acetylthiomethyl with a base.

Reaction Scheme 3

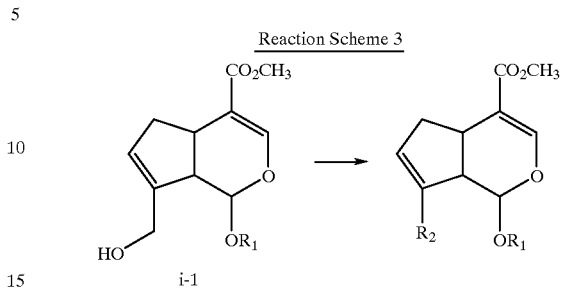

4) As depicted in the following Reaction Scheme 4, the compound of formula (I) wherein $R_1$ is lower alkyl or benzyl, $R_2$ is 2,2-dimethyl-1,3-dioxolan-5-ylmethyloxymethyl, 6-aminofuran-9-ylmethyl, 4-amino-2-hydroxy-5-methylpyrimidin-1-ylmethyl or 2,4-dihydroxy-5-methylpyrimidin-1-ylmethyl, and $R_3$ is methoxycarbonyl can be prepared by replacing the hydroxy group of compound α-i-1 or β-i-1 in Reaction Scheme 1 by bromine, then by reacting the product thus obtained with 2,2dimethyl-1,3-dioxolane-4-methanol, 6-aminofuran, 4-amino-2-hydroxypyrimidine or 2,4-dihydroxy-5-methylpyrimidine each of which are pre-treated with sodium hydride. Also, the compound wherein $R_2$ is 2,3-dihydroxypropyloxymethyl can be prepared by treating the compound wherein $R_2$ is 2,2-dimethyl-1,3dioxolan-5-ylmethyloxymethyl with hydrochloric acid.

Reaction Scheme 4

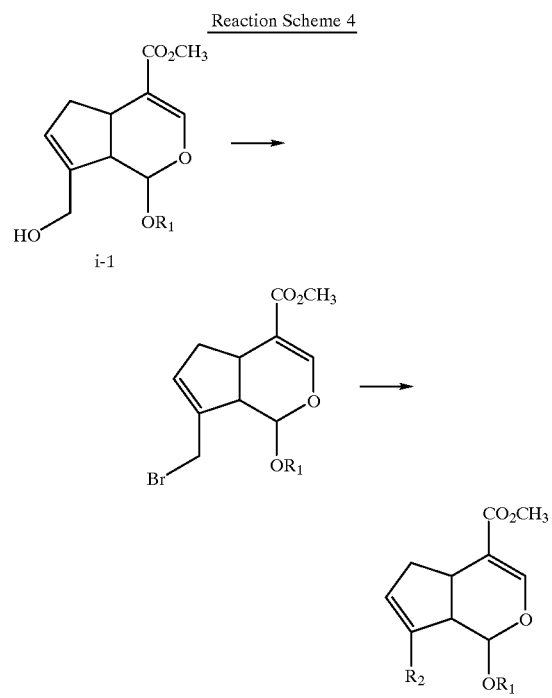

5) As depicted in the following Reaction Scheme 5, the compound of formula (I) wherein $R_1$ is various alkanoyl, $R_2$ is formyl, and $R_3$ is methoxycarbonyl can be prepared by oxidizing the hydroxymethyl group at 7-position of genipin into formyl in the presence of an oxidizing agent to produce the compound i-2 in step 1, then by reacting the product thus obtained with various alkanoyl chloride in the presence of a catalyst in step 2.

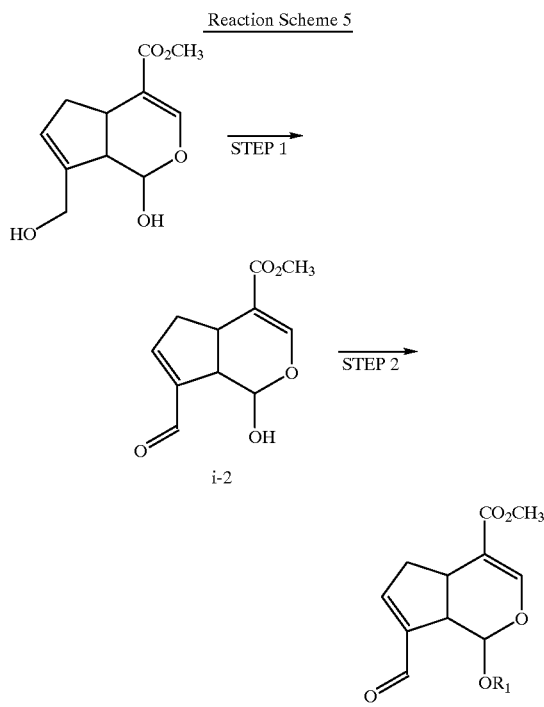

The oxidizing agent mentioned for step 2 reaction of Reaction Scheme 1 can be used in the above step 1 reaction, and pyridine or N,N-dimethylaminopyridine can be used as a catalyst in the above step 2 reaction.

6) As depicted in the following Reaction Scheme 6, the compound of formula (I) wherein $R_1$ is various alkanoyl, $R_2$ is various alkanoyloxymethyl having the same alkanoyl group with $R_1$ and $R_3$ is methoxycarbonyl can be prepared by reacting genipin with the corresponding alkanoyl chloride in the presence of pyridine.

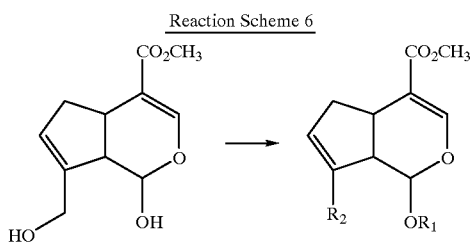

Next, processes for preparing the compound of formula (I) wherein $R_3$ is not methoxycarbonyl are explained.

7) As depicted in the following Reaction Scheme 7, the compound of formula (I) wherein $R_1$ is lower alkyl or benzyl, and $R_2$ and $R_3$ are formyl can be prepared by treating the compound i-1 in Reaction Scheme 1 with sodiumborohydride or diisobutylaluminumhydride to reduce the methoxycarbonyl group into hydroxymethyl group in step 1, then by oxidizing the hydroxymethyl group thus produced into formyl group in the presence of an oxidizing agent in step 2. Herein, the same oxidizing agent as mentioned in step 2 reaction of Reaction Scheme 1 can be used.

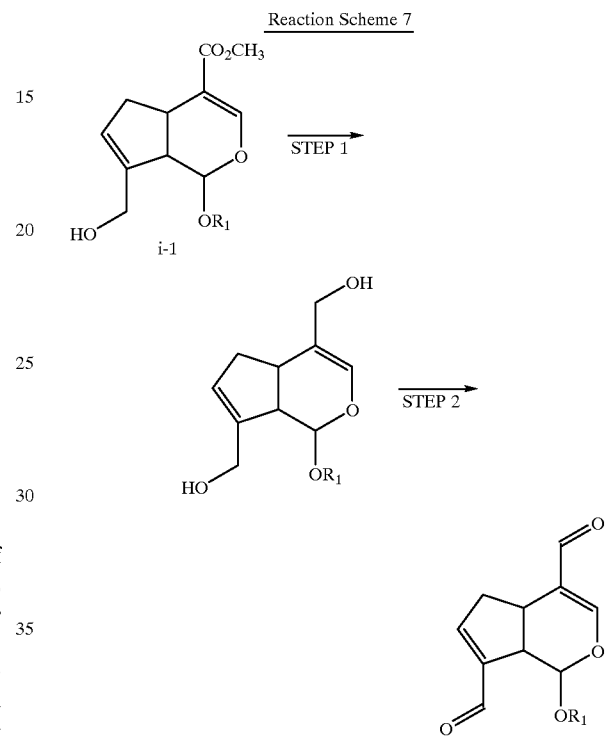

8) As depicted in the following Reaction Scheme 8, the compound of formula (I) wherein $R_1$ is lower alkyl or benzyl, $R_2$ is formyl, and $R_3$ is acetyloxymethyl can be prepared by reacting the compound i-1 with t-butyldimethylsilylchloride to protect the hydroxy group in step 1, reducing the compound thus produced with sodiumborohydride to obtain the compound i-3 wherein 4-position carbon is substituted by hydroxymethyl in step 2, reacting the compound i-3 with acetylchloride in the presence of pyridine in step 3, treating the compound thus obtained with a desilylating agent such as tetrabutylammoniumfluoride (TBAF), etc. to remove the silyl group in step 4, and treating the compound obtained in step 4 with an oxidizing agent in step 5. Herein, the same oxidizing agent as mentioned in step 2 reaction of Reaction Scheme 1 can be used.

Reaction Scheme 8

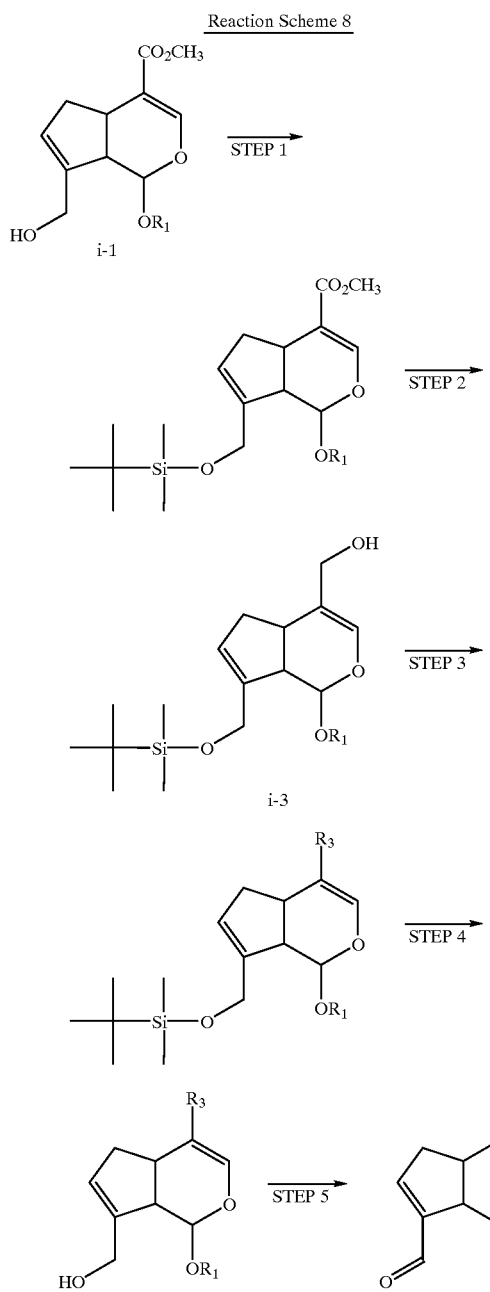

Reaction Scheme 9

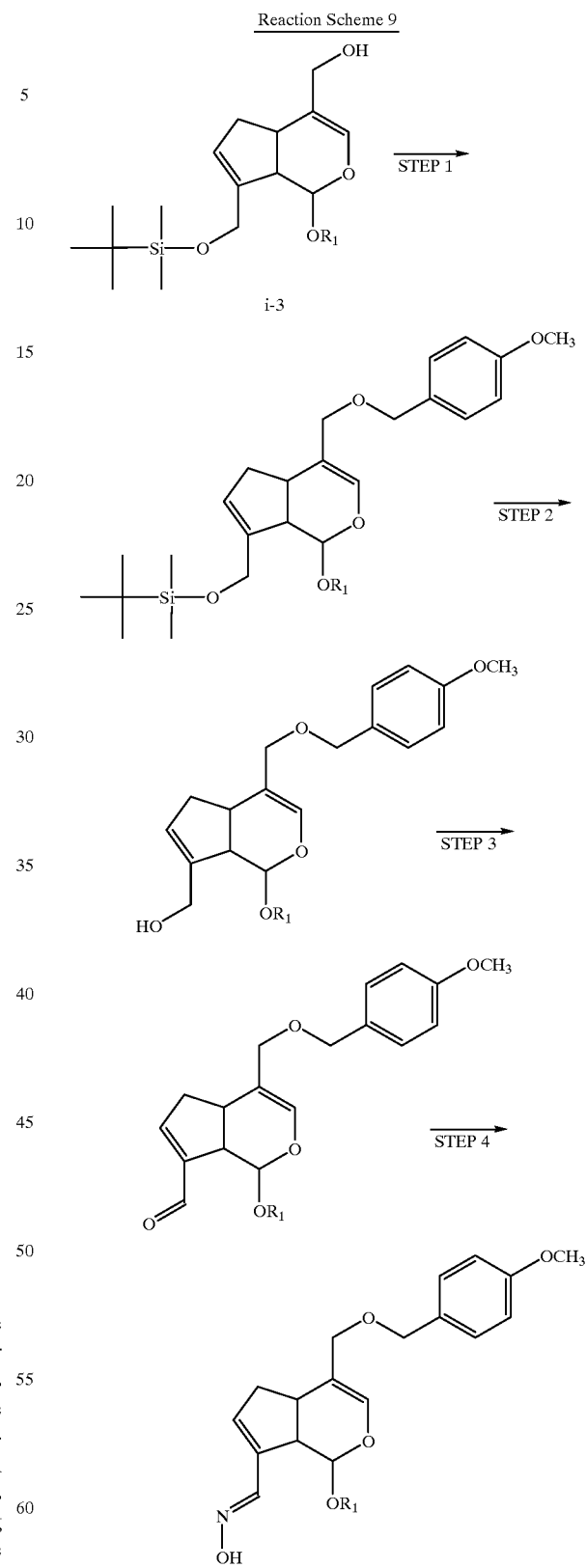

9) As depicted in the following Reaction Scheme 9, the compound of formula (I) wherein $R_1$ is lower alkyl or benzyl, $R_2$ is hydroxyiminomethyl, and $R_3$ is 4-methoxybenzyloxymethyl can be prepared by treating the compound i-3 with p-methoxybenzylchloride after pretreatment using sodiumhydride in step 1, removing the silyl group by a desilylating agent such as tetrabutylamnioniumfluoride(MAF), etc. in step 2, oxidizing the hydroxymethyl group into formyl group in the presence of an oxidizing agent in step 3, and converting the formyl group into hydroxyiminomethyl group by the use of hydroxylamine in step 4. Herein, the same oxidizing agent as mentioned in step 2 reaction of Reaction Scheme 1 can be used.

10) As depicted in the following Reaction Scheme 10, the compound of formula (I) wherein $R_1$ is lower alkyl or benzyl, $R_2$ is hydroxymethyl, and $R_3$ is hydroxyiminomethyl or methoxyiminomethyl can be prepared by oxidizing the hydroxymethyl group at 4-position of compound i-3 into formyl group in the presence of the same oxidizing agent as mentioned in step 2 reaction of Reaction Scheme 1 in step 1, reacting the compound thus obtained with hydroxylamine or methoxyamine to produce a compound wherein $R_3$ is hydroxyiminomethyl or methoxyiminomethyl in step 2, and treating the compound obtained in step 2 with tetrabutylamrnmoiumfluoride(TBAF) as a desilylating agent in step 3.

Reaction Scheme 10

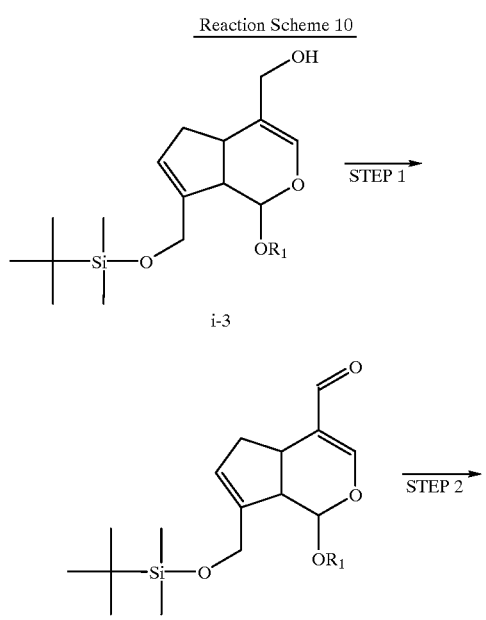

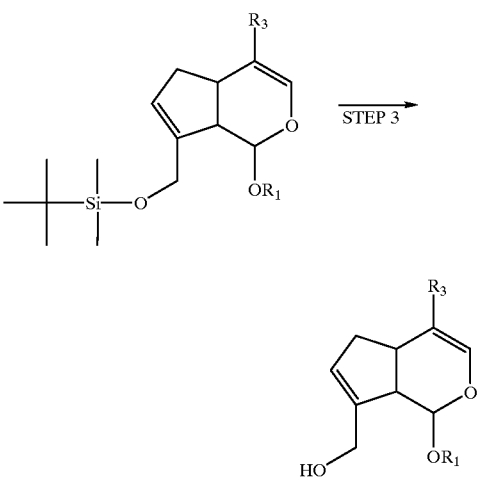

The compound of formula (I) of the present invention can be prepared by processes described above or by processes appropriately combined therefrom. Those processes will be more specifically explained in the following examples.

Typical examples of the compound of formula (I) prepared according to the above processes are listed in the following Table 1.

TABLE 1

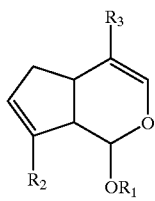

| COM. NO. | $R_1$ | $R_2$ | $R_3$ |
|---|---|---|---|
| 1 | Methyl | Formyl | Formyl |
| 2 | Methyl | Hydroxylminomethyl | 4-Methoxybenzyl-oxymethyl |
| 3 | t-Butylacetyl | t-Butylacetyloxymethyl | Methoxycarbonyl |
| 4 | t-Butylacetyl | Formyl | Methoxycarbonyl |
| 5 | Lauroyl | Lauroyloxymethyl | Methoxycarbonyl |
| 6 | Lauroyl | Formyl | Methoxycarbonyl |
| 7 | Dihydrocinnamoyl | Dihydrocinnamoyl-oxymethyl | Methoxycarbonyl |
| 8 | Dihydrocinnamoyl | Formyl | Methoxycarbonyl |
| 9 | Phenoxyacetyl | Phenoxyacetyloxymethyl | Methoxycarbonyl |
| 10 | Phenoxyacetyl | Formyl | Methoxycarbonyl |
| 11 | Isonicotinoyl | Isonicotinoyloxymethyl | Methoxycarbonyl |
| 12 | Isonicotinoyl | Formyl | Methoxycarbonyl |
| 13 | Benzyl | Formyl | Methoxycarbonyl |
| 14 | Benzyl | Hydroxylminomethyl | Methoxycarbonyl |

The present inventors have also tested the inhibitory effect on HBV replication, cytotoxicity and acute toxicity of the novel genipin based compound of formula (I) according to the present invention in order to identify its anti HBV activity and toxicity.

Inhibitory effect on HBV replication was examined by the use of 2.2.15. cell. 2.2.15. cell line (see, Sells et al., Journal of Virology, 62, 2836–2844, 1988) is a hepatoma cell infected by hepatitis B virus and is a representative standard cell which accurately standardizes all the essential viral characteristics induced by a chronic HBV infection. That is, 2.2.15. cell has some merits such that DNA pattern is stable, replicated virus exists in high level, virus-specific RNA replicate and protein are present in an appropriate size and pattern, the penetrated HBV virion is excreted in high titer, etc. Therefore, it has been recognized as a very suitable cell line which can be used when the anti viral activity of any compound on HBV is evaluated (see, Korba and Milman, Antiviral Research, 15, p217–228, 1991).

First, the present inventors cultured 2.2.15. cell and treated the cell with the novel compound according to the present invention. Then, extraction of DNA and RNA, gel electrophoresis, and hybridization analysis of HBV DNA were carried out to identify the inhibitory activity of the compound of the present invention on HBV replication. Herein, untreated cell was used as a control and ddC (dideoxy cytidine) widely known as a therapeutic agent for hepatitis was used as a comparative compound. As a result, it could be seen that the genipin derivative according to the present invention has an excellent inhibitory effect on replication like the known ddC.

Further, the present inventors have performed cytotoxicity test using the neutral red dye uptake method to determine that the anti viral effect of the compound of formula (I) is due to its general influence on cell growth. As a result, it was identified that the toxicity of the compound of formula (I) is much less than that of ddC. Also, from the acute toxicity test using mouse as the test animal, it could be seen that the compound according to the present invention has a superior safety to the known compound genipin.

Consequently, the compound of formula (I) according to the present invention is safe and has an excellent therapeutic effect for hepatitis B. Therefore, it is another object of the present invention to provide a pharmaceutical composition for the treatment of hepatitis B comprising as an active ingredient the compound of formula (I), as defined above, or its pharmaceutically acceptable salt.

When the pharmaceutical composition according to the present invention is used for clinical purpose, it may be formulated into solid, semi-solid or liquid pharmaceutical preparations for oral or parenteral administration by combining the compound of formula (I) with a pharmaceutically acceptable inert carrier.

The pharmaceutically acceptable inert carrier which can be used for this purpose may be solid or liquid. It may be one or more selected from a group consisting of diluents, flavouring agents, solubilizing agents, lubricants, suspending agents, binders, swelling agents, etc. Specific example of the solid or liquid carrier which may be suitably used in the present invention includes lactose, starch, mannitol, cottonseed oil, etc.

When the active compound of formula (I) of the present invention is used as a medicine for prevention and treatment of hepatitis B, it is preferably administered in an amount of 0.1 to 100 mg per kg of body weight per day at the first stage. However, the administration dosage can be varied with the requirement of the subject patient, severity of the infections to be treated, the selected compound and the like. The prefered dosage suitable for a certain condition can be determined by a person skilled in this art according to a conventional manner. In general, the therapeutic treatment is started from the amount less than the optimal dosage of the active compound and then the administration dosage is increased little by little until the optimal therapeutic effect is obtained. As a matter of convenience, the total daily dosage can be divided into several portions and administered over several times.

The present invention will be more specifically explained by the following examples. However, it should be understood that the examples are intended to illustrate but not to in any manner limit the scope of the present invention.

EXAMPLE 1

Synthesis of (1R,4aS,7aS)-4,7-diformyl-1-metboxy-1,4a,5,7a-tetrahydrocyclopenta-[c]pyran(1)

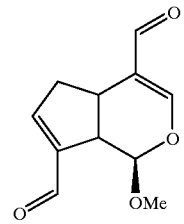

5 g (22.1 mmol) of methyl (4aS,7aS)-1-hydroxy-7-hydroxymethyl-1,4a,5,7a-tetrahydrocyclopenta[c]pyran-4-carboxylate was dissolved in 25 ml of methanol and catalytic amount of trifluoroboron diethylether was added thereto. The reaction mixture was stirred at room temperature for 20 hours and then the reaction was stopped by the addition of saturated aqueous sodium bicarbonate solution. The organic layer was separated, dried over anhydrous magnesium sulfate, filtered, and distilled under vacuum. The residue was purified by silica gel column chromatography (eluent: n-hexane/ethylacetate=5/1, v/v) to obtain 5.26 g (Yield 100%) of methyl (1R,4aS,7aS)-7-hydroxymethyl-1-methoxy-1,4a,5,7a-tetrahydrocyclopenta[c]pyran-4-carboxylate as an oil.

0.15 g (0.62 mmol) of methyl (1R,4aS,7aS)-7-hydroxymethyl- 1-methoxy-1,4a,5,7a-tetrahydrocyclopenta[c]pyran4-carboxylate thus obtained was dissolved in 6 ml of dried tetrahydrofuran and then the resulting solution was cooled down to −78° C. under nitrogen atmosphere. 2.7 ml (4.11 mmol) of diisobutylaluminum hydride (1.5M in toluene) was slowly added dropwise thereto and the resulting mixture was stirred for 3 hours while its temperature being slowly raised to room temperature. Methanol was introduced to the solution to stop the reaction and then saturated aqueous sodium sulfate solution and silica gel were added thereto. The whole mixture was stirred for 30 minutes and filtered through diatomaceous earth, then the filtrate was concentrated to obtain 0.11 g (0.49 mmol) of (1R,4aS,7aS)-4,7-dihydroxymethyl-1-methoxy-1,4a,5,7a-tetrahydrocyclopenta[c]pyran as a colorless oil.

After 0.11 g (0.49 mmol) of (1R,4aS,7aS)-4,7-dihydroxymethyl-1-methoxy-1,4a,5,7a-tetrahydrocyclopenta[c]pyran was dissolved in 5 ml of methylene chloride, 0.608 g (2.82 mmol) of pyridiniumchlorochromate was added thereto and the resulting mixture was stirred overnight. The reaction mixture was filtered through diatomaceous earth and the filtrate was concentrated. The residue was subjected to silica gel column chromatography (eluent: n-hexane/ethylacetate=3/1, v/v) to obtain 0.03 g (Yield 30%) of the title compound as a colorless oil.

$^1$H NMR (CDCl$_3$): δ2.55–2.70(m,1H), 2.90–3.05(m,1H), 3.35–3.40(m,2H), 3.50 (s,3H), 5.60(d,1H,J=1.98 Hz), 6.95 (d,1H,J=2.77 Hz), 7.20(s,1H), 7.30 (s,1H), 9.30 (s,1H), 9.80(s,1H); $^{13}$C NMR (CDCl$_3$): δ31.46, 38.70, 45.85, 57.13, 99.73, 123.41, 144.19, 156.13, 162.37, 189.74, 191.01; ESIMS(Electron Spray Impact Mass Spectrometer): 230 (M+Na)$^+$, 308, 338, 369, 439(2M+Na)$^+$(base peak), 470; IR (KBr): 2950, 2830, 1680, 1635cm$^{-1}$.

EXAMPLE 2

Synthesis of (1R,4aS,7aS)-7-hydroxyiminomethyl-1-methoxy-4-(p-methoxybenzyloxymethyl )-1,4a,5, 7a-tetrahydrocyclopenta[c]pyran(2)

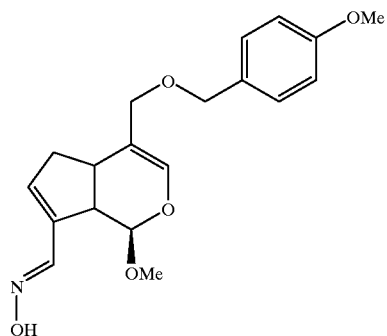

3 g (12.5 mmol) of methyl (1R,4aS,7aS)-7-hydroxymethyl-1-methoxy-1,4a,5,7a-tetrahydrocyclopenta[c]pyran4-carboxylate was dissoved in 50 ml of dimethylformamide and 1.9 ml (13.8 mmol) of triethylamine was added thereto under nitrogen atmosphere. The reaction solution was stirred for one hour and then 2.07 g (13.8 mmol) of t-butyldimethylsilylchloride dissolved in 10 ml of dimethylformamide was added dropwise thereto. After stirring for 3 hours, 1N-aqueous hydrochloric acid solution was added in order to stop the reaction. Organic layer was extracted by the addition of diethylether and then it was washed with saturated aqueous sodium bicarbonate solution and saturated saline solution. The organic layer was dried over anhydrous magnesium sulfate, filtered, and concentrated to obtain 4.16 g (Yield 94%) of methyl (1R,4aS,7aS)-7-(t-butyldimethylsilyloxymethyl)-1 -methoxy-1,4a,5,7a-tetrahydrocyclo penta[c]pyran-4-carboxylate as a colorless oil.

4.16 g (11.7 mmol) of methyl (1R,4aS,7aS)-7-(t-butyldimethylsilyloxymethyl)-1-methoxy-1,4a,5 ,7a-tetrahydrocyclopentat[c]pyran-4-carboxylate thus obtained was dissolved in 100 ml of tetrahydrofuran and then the resulting solution was cooled down to −78° C. under nitrogen atmosphere. 19.55 ml (29.33 mmol) of diisobutylamoniurnhydride (1.5M in toluene) was slowly added thereto and the reaction solution was stirred for 30 minutes. The solution was stirred for ether 3 hours while its temperature being raised to room temperature. Methanol was introduced to the solution to stop the reaction and then saturated aqueous sodium sulfate solution and silica gel were added thereto. The mixture was stirred for 30 minutes and filtered through diatomaceous earth. Then, the filtrate was concentrated to obtain 3.45 g (Yield 90%) of (1R,4aS,7aS)-7-(t-butyldimethylsilyloxymethyl)-4-hydroxymethyl-1-methoxy-1,4a,5, 7a-tetrahydrocyclopenta[c]pyran as a colorless oil.

0.402 g (10.04 mmol) of sodium hydride was introduced into a reaction vessel and 10ml of dried dimethylformanide was added thereto under nitrogen atmosphere. After the reaction temperature was lowered to 5° C., 3 g (8.37 mmol) of (1R,4aS,7aS)-7-(t-butyldimethylsilyloxymethyl)-4-hydroxymethyl-1-methoxy-1,4a,5,7a-tetrahydrocyclopenta[c]pyran which is diluted in advance in 20 ml of dried dimethylfor- mamide was slowly added dropwise thereto. After stirring for one hour, 1.36 ml (10.04 mmol) of p-methoxybenzylchloride was added to the solution, which was then stirred for 6 hours while its temperature being slowly raised to room temperature. Saturated aqueous sodium bicarbonate solution was added to stop the reaction. The reaction solution was extracted with diethylether and saturated saline solution, dried over anhydrous magnesium sulfate, filtered and concentrated. The residue was subjected to silica gel column chromatography (eluent: n-hexane/ethylacetate=8/1, v/v) to obtain 1.578 g (Yield 42.2%) of (1R,4aS,7aS)-7-(t-butyldimethylsilyloxymethyl)-1-methoxy-4-(p-methoxybenzyloxymethyl)-1,4a,5,7a-tetrahydrocyclopenta[c]pyran as a colorless oil.

1.578 g (3.53 mmol) of (1R,4aS,7aS)-7-t-butyldimethylsilyloxymethyl)-1-methoxy-4-(p-methoxybenzyloxymethyl)-1,4a,5,7a-tetrahydrocyclopenta[c]pyran was dissolved in 13 mg of tetrahydrofuran and then 3.8 ml (3.89 mmol) of tetrabutylammoniumfluoride (1M in THF) was added thereto. After stirring for 2 hours, the reaction was stopped by adding saturated aqueous sodium bicarbonate solution. The reaction solution was extracted with diethylether and saturated saline solution, dried over anhydrous magnesium sulfate, filtered, and concentrated. The residue was subjected to silica gel column chromatography (eluent: n-hexane/ethylacetate=3/1, v/v) to obtain 0.821 g (Yield 70%) of (1R,4aS,7aS)-7-hydroxymethyl-1-methoxy-4-(p-methoxybenzyloxymethyl)- 1,4a,5,7a-tetrahydrocyclopenta[c]pyran as a colorless oil.

0.240 g (0.72 mmol) of (1R,4aS,7aS)-7-hydroxymethyl-1-methoxy4-(p-methoxybenzyloxymethyl)-1,4a,5,7a-tetrahydrocyclopenta[c]pyran was dissolved in 5 ml of methylene chloride and 0.311 g (1.44 mmol) of pyridiniumchlorochromate was added thereto. The reaction solution was stirred for one hour, filtered through diatomaceous earth, and then concentrated. The residue was subjected to silica gel column chromatography (eluent: n-hexanelethylacetate=4/1, v/v) to obtain 0.167 g (Yield 70%) of (1R,4aS,7aS)-7-formyl-1-methoxy-4-(p-methoxybenzyloxymethyl)-1,4a,5,7a-tetrahydrocyclopenta[c]pyran as a colorless oil.

0.064 g (0.92 mmol) of hydroxylamine hydrochloride was dissolved in 3 ml of ethanol and the resulting solution was neutralized by the addition of 0.15 mlk (1.10 mmol) of triethylaine. 0.152 g (0.46 mmol) of (1R,4aS,7aS)-7-formyl-1-methoxy-4-(p-methoxybenzyloxymethyl)-1,4a,5,7a-tetrahydrocyclopenta[c]pyran was diluted in 1 ml of ethanol and the mixture thus obtained was added dropwise to the above solution. The whole mixture was stirred for one hour and concentrated. The residue was extracted with ethylacetate and saturated saline solution, dried over anhydrous magnesium sulfate, filtered, and concentrated. The residue was subjected to silica gel column chromatography (eluent: n-hexane/ethylacetate=4/1, v/v) to obtain 0.12 g (Yield 75%) of the title compound as a white solid.

¹H NMR (CDCl₃): δ2.15–2.30(m,1H), 2.55–2.70(m,1H), 2.90–3.05(m,2H), 3.40 (s,3H), 3.72(s,3H), 3.80(d,1H,J=11.67 Hz), 3.85(d,1H,J=11.67 Hz), 4.30 (dd,2H,J=11.43, 27.82 Hz), 4.70(d,1H,J=6.1 Hz), 6.15(s,1H), 6.30(s,1H), 6.70–6.80(m,2H), 7.10–7.20(m,2H), 7.85(s,1H), 8.30(bs, 1H); ¹³C NMR (CDCl₃): δ37.03, 38.44, 46.87, 55.69, 57.01, 69.80, 70.98, 101.08, 114.20, 114.38, 129.84, 130.81, 137.83, 139.17, 140.25, 147.66, 159.55.

EXAMPLE 3

Synthesis of Methyl (1S,4aS,7aS)-1-t-butylacetyloxy-7-t-butylacetyloxymethyl-1,4a, 5,7a-tetrahydrocyclopenta[c]pyran-4-carboxylate(3)

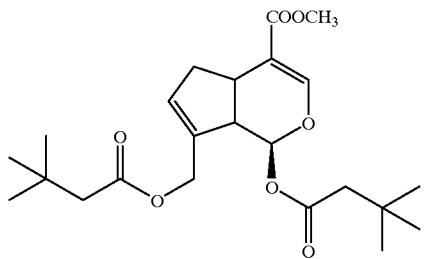

0.1 g (0.44 mmol) of methyl (4aS,7aS)-1-hydroxy-7-bydroxymethyl-1,4a, 5,7a-tetrahydrocyclopenta[c]pyran-4-carboxylate was dissolved in 5 ml of dried metlylene chloride, then 0.17 ml (2.12 mmol) of pyridine and 0.24 ml (1.77 mmol) of t-butylacetylchloride were added thereto in order. The resulting mixture was stirred for 3 hours at room temperature and concentrated. The residue was dissolved in ethylacetate and saturated aqueous sodium bicarbonate solution was added thereto. After the solution was stirred for 2 hours, the ethylacetate layer was separated. This organic layer was washed with saturated saline solution, dried over anhydrous magnesium sulfate, filtered, and concentrated. The residue was subjected to silica gel column chromatography (eluent: n-hexane/ethylacetate=5/1, v/v) to obtain 0.1 5 g (Yield 81%) of the title compound as a white solid.

¹H NMR (CDCl₃): δ1.61(s,9H), 1.07(s,9H), 2.20–2.24(m, 1H), 2.25(s,2H), 2.26(d,1H,J=13.8 Hz), 2.33(d,1H,J=13.8 Hz), 2.88–2.96(m,2H), 3.25–3.33 (m,1H), 3.75(s,3H), 4.62 (d,1H,J=13.6 Hz), 4.70(d,1H,J=13.6 Hz), 5.89 (s,1H), 5.86 (bs, 1H), 7.45(s,1H);

¹³C NMR (CDCl₃): δ29.90, 30.05, 31.16, 31.28, 34.84, 39.00, 45.71, 47.90, 48.25, 51.73, 61.77, 91.64, 111.65, 132.98, 137.08, 152.18, 167.69, 170.91, 172.29; ESIMS: 445(M+Na).

EXAMPLE 4

Syntesis of Methyl (1S,4aS,7aS)-1-t-butylacetyloxy-7-formyl-1,4a,5,7a-tetrahydrocyclopenta[c]pyran-4-carboxylate(4)

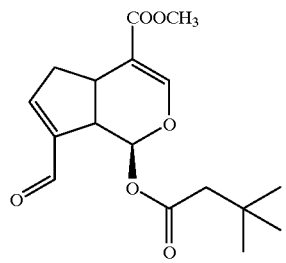

0.5 g (2.21 mmol) of methyl (4aS,7aS)-1-hydroxy-7-hydroxymethyl-1,4a, 5,7a-tetrahydrocyclopenta[c]pyran4carboxylate was dissolved in 10 ml of dried methylene chloride, then 0.954 g (4.42 mmol) of pyridiniumchlorochromate was added thereto. The reaction solution was stirred for 3 hours, filtered through cellite and then the filtrate was concentrated. The residue was subjected to silica gel column chromatography (eluent: n-hexane/ethylacetate=2/1, v/v) to obtain 0.376 g (Yield 76%) of methyl (4aS,7aS)-7-formyl-1-hydroxy-1,4a,5,7a-tetrahydrocyclopenta[c]pyran-4-carboxylate.

0.20 g (0.89 mmol) of methyl (4aS,7aS)-7-formyl-1-hydroxy-1,4a,5,7a-tetrahydrocyclopenta[c]pyran-4-carboxylate thus obtained was dissolved in 5 ml of dried methylene chlroride. 0.17 ml (2.12 mmol) of pyridine and 0.25 ml (1.89 mmol) of t-butylacetylchloride were added thereto in order. The resulting mixture was stirred for 3 hours at room temperature and then concentrated. The residue was dissolved in ethylacetate and saturated aqueous sodium bicarbonate solution was added thereto. After the solution was stirred for 2 hours, the ethylacetate layer was separated. This organic layer was washed with saturated saline solution, dried over anhydrous magnesium sulfate, filtered, and concentrated. The residue was subjected to silica gel column chromatography (eluent: n-hexane/ethylacetate=5/1, v/v) to obtain 0.124 g (Yield 43%) of the title compound as a white solid.

¹H NMR (CDCl₃) δ1.05(s,9H), 2.24(d,1H,J=13.8 Hz), 2.31(d,1H,J=13.8 Hz), 2.59–2.66(m,1H), 3.08(m,1H), 3.32–3.42(m,2H), 3.77(s,3H), 6.48(d,1H, J=5.02 Hz), 7.06 (s,1H), 7.48(s,1H), 9.76(s,1H); ¹³C NMR (CDCl₃): δ29.89, 31.19, 34.05, 40.01, 44.22, 47.85, 51.82, 89.67, 110.90, 144.44, 152.58, 155.91, 167.43, 170.81, 189.02; ESIMS: 345(M+Na).

EXAMPLE 5

Synthesis of Methyl (1S,4aS,7aS)-1-lauroyloxy-7-lauroyloxymethyl-1,4a,5,7a-tetrahydrocyclopenta[c]pyran4-carboxylate(5)

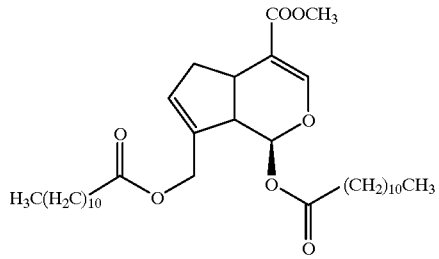

0.2 g (0.88 mmol) of methyl (4aS,7aS)-1-hydroxy-7-hydroxymethyl-1,4a,5,7a-tetrahydrocyclopenta[c]pyran4-carboxylate was dissolved in 5 ml of dried methylene chlroride. 0.36 ml (4.42 mmol) of pyridine and 1.02 ml (4.42 mmol) of lauroylchloride were added thereto in order, and the resulting mixture was stirred overnight. Saturated aqueous sodium bicarbonate solution was added to the mixture to stop the reaction and the mixture was washed with saturated saline solution. The organic layer was dried over anhydrous magnesium sulfate, filtered, and concentrated. The residue was subjected to silica gel column chromatography (eluent: n-hexane/ethylacetate=9/1, v/v) to obtain 0.416 g (Yield 80%) of the title compound.

$^1$H NMR (CDCl$_3$): δ0.80(m,3H), 1.10–1.32(m,32H), 2.15 (m,1H), 2.20–2.35(m, 4H), 2.82(m,2H), 3.20(m,1H), 3.65 (s,3H), 4.50(d,1H,J=13.4 Hz), 4.60(d, 1H,J=13.6 Hz), 5.75–5.89(d,s,2H,J=7.3 Hz), 7.38(s, 1H);

$^{13}$C NMR (CDCl$_3$): δ14.43, 23.04, 24.92, 25.34, 29.40, 29.54, 29.60, 29.63, 29.69, 29.80, 29.84, 29.97, 32.28, 34.56, 34.61, 35.06, 39.05, 45.72, 51.65, 61.93, 92.06, 111.69, 132.81, 137.27, 152.09, 167.63, 172.44, 173.70, 186.12; ESIMS: 613(M+Na).

EXAMPLE 6

Synthesis of Methyl (1S,4aS,7aS)-7-formyl-1-lauroyloxy-1,4a,5,7a-tetrahydrocyclopenta[c]pyran-4-carboxylate(6)

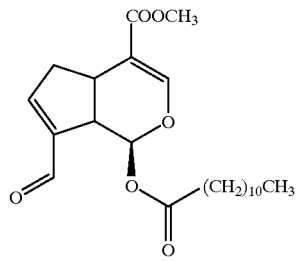

0.1 g (0.45 mmol) of methyl (4aS,7aS)-7-formyl-1-hydroxy-1,4a,5,7a-tetrahydrocyclopenta[c]pyran4-carboxylate was dissolved in 3 ml of dried methylene chlroride. 0.09 ml (1.13 mmol) of pyridine and 0.29 ml (1.13 mmol) of lauroylchloride were added thereto in order, and the resulting mixture was stirred overnight. Then, saturated aqueous sodium bicarbonate solution was added to the mixture to stop the reaction and the mixture was washed with saturated saline solution. The organic layer was dried over anhydrous magnesium sulfate, filtered, and concentrated. The residue was subjected to silica gel column chromatography (eluent: n-hexane/ethylacetate=3/1, v/v) to obtain 0.124 g (Yield 68%) of the title compound.

$^1$H NMR (CDCl$_3$): δ0.80(m,3H), 1.10–1.30(m,18H), 2.25 (m,2H), 2.50(m,1H), 3.00(m,1H), 3.15(m,1H), 3.30(m,1H), 3.68(s,3H), 6.25(d,1H,J=5.7 Hz), 6.92(d,1H,J=1.2 Hz), 7.38 (s,1H), 9.70(s,1H); $^{13}$C NMR (CDCl$_3$) δ14.44, 23.04, 24.86, 29.38, 29.58, 29.69, 29.80, 29.95, 32.27, 34.44, 34.49, 40.11, 43.98, 51.75, 90.33, 110.87, 144.72, 152.52, 155.70, 167.39, 172.41, 188.81; ESIMS: 429(M+Na); IR(KBr) 2950, 2860, 1770, 1720, 1700, 1660 cm$^{-1}$.

EXAMPLE 7

Synthesis of Methyl (1S,4aS,7aS)-1-dihydrocinnamoyloxy-7-dihydrocinnamoyloxymethyl-1,4a,5,7a-tetrahydrocyclopenta[c]pyran-4-carboxylate(7)

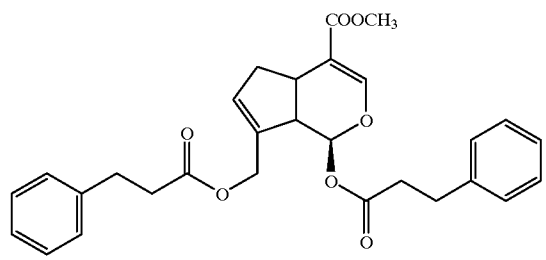

0.2 g (0.88 mmol) of methyl (4aS,7aS)-1-hydroxy-7-hydroxymethyl-1,4a,5,7a-tetrahydrocyclopenta[c]pyran4-carboxylate was dissolved in 5 ml of dried methylene chlroride. 0.36 ml (4.42 mmol) of pyridine and 0.66 ml (4.42 mmol) of dihydrocinnamoylchloride were added thereto in order, and the resulting mixture was stirred for 3 hours. Then, saturated aqueous sodium bicarbonate solution was added to the mixture to stop the reaction and the mixture was washed with saturated saline solution The organic layer was dried over anhydrous magnesium sulfate, filtered, and concentrated. The residue was subjected to silica gel column chromatography (eluent: n-hexane/ethylacetate=5/1, v/v) to obtain 0.354 g (Yield 82%) of the title compound.

$^1$H NMR (CDCl$_3$): δ2.20(m,1H), 2.60–2.80(m,5H), 2.80–2.95(m,1H), 2.95–3.10 (m,4H), 3.25(m,1H), 3.75(s, 3H), 4.58(d,1H,J=13.5 Hz), 4.65(d,1H,J=13.5 Hz), 5.82(s, 2H), 5.90(d,1H,J=7 Hz), 7.15–7.22(bs,6H), 7.22–7.40 (m,4H), 7.45(s,1H); $^{13}$C NMR (CDCl$_3$): δ25.64, 26.04, 29.58, 30.81, 40.43, 46.43, 55.732, 86.80, 106.50, 121.44, 121.56, 123.42, 123.64, 123.70, 127.84, 131.70, 135.07, 135.47, 146.74, 162.33, 166.35, 167.47; ESIMS: 513(M+Na).

EXAMPLE 8

Synthesis of Methyl (1S,4aS,7aS)-1-dihydrocinnamoyloxy-7-formyl-1,4a,5,7a-tetra-hyhdrocyclopenta[c]pyran-4-carboxylate(8)

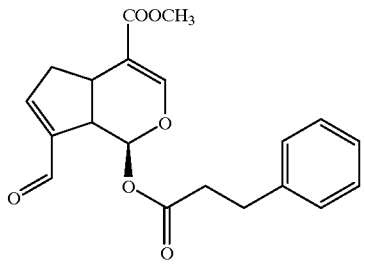

0.3 g (1.34 mmol) of methyl (4aS,7aS)-7-formyl-1-hydroxy-1,4a,5,7a-tetrahydrocyclopenta[c]pyran-4-carboxylate was dissolved in 5 ml of dried methylene chlroride. 0.27 ml (3.35 mmol) of pyridine and 0.5 ml (3.35 mmol) of dihydrocinnamoylchloride were added thereto in order, and the resulting mixture was stirred for 3 hours. Then, saturated aqueous sodium bicarbonate solution was added to the mixture to stop the reaction and the mixture was washed with saturated saline solution. The organic layer was dried over anhydrous magnesium sulfate, filtered, and concentrated. The residue was subjected to silica gel column chromatography(eluent: n-hexane/ethylacetate=3/1, v/v) to obtain 0.358 g (Yield 75%) of the title compound.

$^1$H NMR (CDCl$_3$): δ2.60(m,1H), 2.65–2.80(m,2H), 2.90–3.00(m,2H), 3.10 (m,1H), 3.25(m,1H), 3.75(s,3H), 6.40(d,1H,J=5.4 Hz), 7.00(s,1H), 7.15–7.25(m,3H), 7.25 –7.35(m,2H), 7.42(s,1H), 9.75(s,1H)

$^{13}$C NMR (CDCl$_3$) δ30.86, 34.24, 35.98, 40.07, 43.98, 51.77, 90.38, 110.91, 126.71, 128.89, 140.43, 144.58, 152.42, 155.78, 167.34, 171.52, 188.87; ESIMS: 379(M+ Na).

EXAMPLE 9

Synthesis of Methyl (1S,4aS,7aS)-1-phenoxyacetyloxy-7-phenoxyacetyloxmethyl-1,4a,5,7a-tetrahydrocyclopenta[c]pyran4-carboxylate(9)

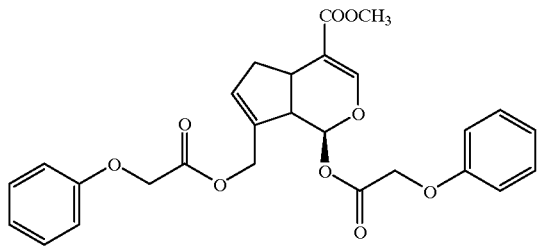

0.1 g (0.44 mmol) of methyl (4aS,7aS)-1-hydroxy-7-hydroxymethyl-1,4a,5,7a-tetrahydrocyclopenta[c]pyran-4-carboxylate was dissolved in 3ml of dried methylene chl-roride. 0.18 ml (2.22 mmol) of pyridine and 0.31 ml (2.22 mmol) of phenoxyacetylchloride were added thereto in order, and the resulting mixture was stirred overnight. Then, saturated aqueous sodium bicarbonate solution was added to the mixture to stop the reaction and the mixture was washed with saturated saline solution. The organic layer was dried over anhydrous magnesium sulfate, filtered, and concentrated. The residue was subjected to silica gel column chromatography (eluent: n-hexane/ethylacetate=5/1, v/v) to obtain 0.164 g (Yield 75%) of the title compound.

$^1$H NMR (CDCl$_3$): δ2.15(m,1H), 2.70–2.88(m,2H), 3.15 (m,1H), 3.65(s,3H), 4.50–4.78(m,6H), 5.85(s,1H), 5.95(d, IH,J=6.7Hz), 6.75–6.85(m,4H), 6.85–7.00(m, 2H), 7.10–7.25(m,2H), 7.35(s,1H) $^{13}$C NMR (CDCl$_3$): δ34.63, 39.02, 45.81. 51.72, 62.49, 62.65, 92.38, 111.98, 115.08, 115.17, 122.22, 122.41, 129.97, 130.01, 134.58, 136.02, 151.62, 158.02, 158.18, 167.33, 167.96, 169.02; ESIMS: 517(M+Na).

EXAMPLE 10

Synthesis of Methyl (1S,4aS,7aS)-7-formyl-1-phenoxyacetyloxy-1,4a,5,7a-tetra-hydrocyclopenta[c]pyran-4-carboxylate(10)

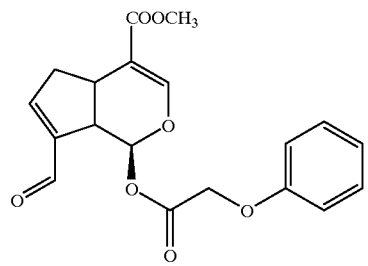

0.2 g (0.89 mmol) of methyl (4aS,7aS)-7-formyl-1-hydroxy-1,4a,5,7a-tetrahydrocyclopenta[c]pyran-4-carboxylate was dissolved in 5 ml of dried methylene chlroride. 0.18 ml (2.22 mmol) of pyridine and 0.31 ml (2.22 mmol) of phenoxyacetyichioride were added thereto in order, and the resulting mixture was stirred overnight. Then, saturated aqueous sodium bicarbonate solution was added to the mixture to stop the reaction and the mixture was washed with saturated saline solution. The organic layer was dried over anhydrous magnesium sulfate, filtered, and concentrated. The residue was subjected to silica gel column chromatography (eluent: n-hexane/ethylacetate=3/1, v/v) to obtain 0.21 7 g (Yiel d 68%) of the title compound.

$^1$H NMR (CDCl$_3$) δ2.58(m,1H), 3.10(m,1H), 3.35(m, 2H), 3.75(s,3H), 4.70(s, 2H), 6.50(d,1H,J=4.7 Hz), 6.85–6.95(m,2H), 6.95–7.00(m,1H), 7.25–7.35 (m,2H), 7.40(s,1H), 9.75(s,1H);

$^{13}$C NMR (CDCl$_3$): δ34.02, 40.04, 44.10, 51.79, 65.47, 90.72, 116.17, 115.12, 122.26, 129.93, 144.23, 151.99, 156.17, 158.05, 167.11, 167.79, 189.04; ESIMS: 381(M+ Na); IR(KBr): 2950, 2860, 1780, 1720, 1685 cm$^{-1}$.

EXAMPLE 11

Synthesis of Methyl (1S,4aS,7aS)-1-isonicotinoyloxy-7-isonicotinoyloxymethyl-1,4a,5,7a-tetrahydrocyclopenta[c]pyran4-carboxylate(11)

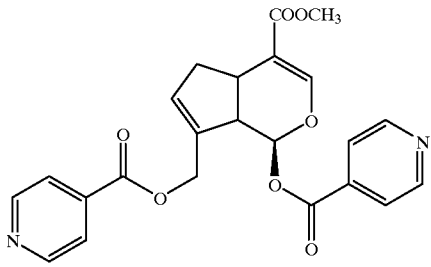

0.10 g (0.44 mmol) of methyl (4aS,7aS)-1-hydroxy-7-hydroxymethyl-1,4a,5,7a-tetrahydrocyclopenta[c]pyran-carboxylate was dissolved in 5 ml of methylene chlroride. 0.24 g (1.32 mmol) of isonicotinoylchloride hydrochloride and 1.2 ml (15 mmol) of pyridine were added thereto, and the resulting mixture was stirred overnight. The reaction mixture was concentrated and the residue was dissolved in ethylacetate. Saturated aqueous sodium bicarbonate solution was added thereto and the mixture was stirred for 2 hours. The ethylacetate layer was separated, washed with saturated saline solution, dried over anhydrous magnesium sulfate, filtered, and concentrated. The residue was subjected to silica gel column chromatography [eluent: (i) n-hexane/ethylacetate=4/1, v/v; (ii) 2% triethylamine in ethylacetate solution] to obtain 0.096 g (Yield 50%) of the title compound as a white solid.

$^1$H NMR (CDCl$_3$): δ2–34–2.42(m,1H), 2.98–3.06(m,1H), 3.17–3.22(m,1H) 3.43–3.53(m,1H), 3.78(s,3H), 4.93(d,1H, J=13.10 Hz), 5.03(d,1H,J=13.10 Hz), 6.13(s,1H), 6.34(d, 1H,J=6.45 Hz), 7.52(s,1H), 7.80–7.87(m,4H), 8.79–8.81(m, 4H);

$^{13}$C NMR (CDCl$_3$): δ34.65, 39.11, 46.46, 51.91, 63.31, 92.79, 112.00, 123.16, 123.26, 135.54, 135.79, 136.31, 137.26, 151.10, 151.27, 151.78, 163.88, 165.10, 167.40; ESIMS: 437(M+1).

EXAMPLE 12

Synthesis of Methyl (1S,4aS,7aS)-7-formyl-1-isonicotinoyloxn-1,4a,5,7a-tetrahydro-cyclopentafclpyran-4-carboxylate(12)

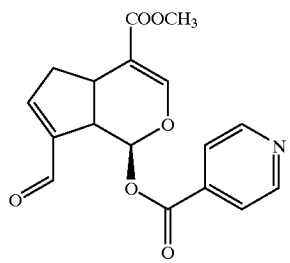

0.1 g (0.45 mmol) of methyl (4aS,7aS)-7-formyl-1-hydroxy-1,4a,5,7a-tetrahydrocyclopenta[c]pyran4- carboxylate was dissolved in 5 ml of dried methylene chlroride. 0.087ml (1.08 mmol) of pyridine and 0.16 g (0.9 mmol) of isonicotinoylchloride hydrochloride were added thereto in order, and the resulting mixture was stirred overnight at room temperature. The reaction mixture was concentrated and the residue was dissolved in ethylacetate. Saturated aqueous sodium bicarbonate solution was added thereto and the mixture was stirred for 2 hours. The ethylacetate layer was separated, washed with saturated saline solution, dried over anhydrous magnesium sulfate, filtered, and concentrated. The residue was subjected to silica gel column chromatographyfeluent[(i) n-hexane/ethylacetate=1/4, v/v; (ii) 0.5% triethylamine in ethylacetate solution] to obtain 0.106 g (Yield 71%) of the title compound as a white solid.

$^1$H NMR (CDCl$_3$): δ2.62–2.71(m,1H), 3.15–3.25(m,1H), 3.49–3.52(m,2H), 3.79 (s,3H), 6.56(dd,1H,J=6.38,11.65 Hz), 7.11l(s,1H), 7.53(s,1H), 7.93(d,2H, J=5.92 Hz), 8.85 (d,2H,J=5.92 Hz), 9.80(s,1H).

EXAMPLE 13

Synthesis of Methyl (1R,4aS,7aS)-1-benzyloxy-7-formyl-1,4a,5,7a-tetrahydrocyclopenta[c]pyran-4-carboxylate(13)

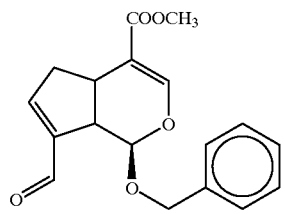

1.13 g (5.0 mmol) of methyl (4aS,7aS)-1-hydroxy-7-hydroxymethyl-1,4a,5, 7a-tetrahydrocyclopenta[c]pyran-4-carboxylate was dissoved in 10 ml of dried tetrahydrofuran, then 2.60 ml (25 mmol) of benzyl alcohol and catalytic amount of trifluoroboron diethylether were added thereto. The resulting mixture was stirred while refluxing for 48 hours at 75° C. The mixture was cooled down to room temperature and concentrated. The residue was dissolved in ethylacetate and then washed with saturated aqueous sodium bicarbonate solution and saturated saline solution The organic layer was dried over anhydrous magnesium sulfate, filtered, and concentrated. The residue was purified by silica gel column chromatography (eluent: n-hexanelethylacetate= 2/1, v/v) to obtain 0.61 g (Yield 39%) of methyl (1R,4aS, 7aS)-1-benzyloxy-7-hydroxymethyl-1,4a,5,7a-tetrahydrocyclopenta[c]pyran-4-carboxylate as an oil.

After 0.59 g (1.86 mmol) of methyl (1R,4aS,7aS)-1-benzyloxy-7-hydroxymethyl-1,4a,5,7a-tetrahydrocyclopenta[c]pyran-4-carboxylate thus obtained was dissolved in 10 ml of dried methylene chloride, 0.81 g (3.76 mmol) of pyridiniumchlorochromate was added thereto and the resulting mixture was stirred for 3 hours at room temperature. The reaction mixture was filtered through cellite and the filtrate was concentrated. The residue was subjected to silica gel column chromatography (eluent: n-hexane/ethylacetate=5/1, v/v) to obtain 0.55 g (Yield 94%) of the title compound as a pale yellow oil.

$^1$H NMR (CDCl$_3$): δ2.57–2.59(m1H), 2.97–3.00(m,1H), 3.36–3.40(m,2H), 3.75(s,3H), 4.65(d,1H,J=11.88 Hz), 4.87 (d,1H,J=11.88 Hz), 5.45(d,1H, J=4.12 Hz), 6.98 (bs,1H), 7.29–7.34(m,5H), 7.50(s,1H), 9.77(s,1H);

$^{13}$C NMR(CDCl$_3$): δ34.09, 39.98, 45.49, 51.67, 71.04, 97.50, 111.02, 128.17, 128.27, 128.82, 137.36, 144.92, 152.69, 155.16, 167.82, 189.52.

EXAMPLE 14

Synthesis of Methyl (1R,4aS,7aS)-1-benzyloxy-7-hydroxyiminomethyl-1,4a,5,7a-tetrahydrocyclopenta[c]pyran-4-carboxylate(14)

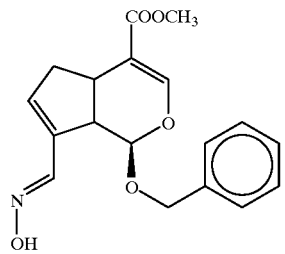

After 0.1 g (0.32 mmol) of methyl (1R,4aS,7aS)-1-benzyloxy-7-formyl-1,4a,5,7a-tetrahydrocyclopenta[c]pyran-4-carboxylate prepared in Example 13 was dissolved in 2 ml of absolute ethanol, 0.1 ml (0.76 mmol) of triethylamine and 0.046 g (0.64 mmol) of hydroxylamine hydrochloride were added thereto. The resulting mixture was stirred for 3 hours at room temperature and then concentrated. The residue was dissolved in ethylacetate and washed with 1N aqueous hydrochloric acid solution, saturated aqueous sodium bicarbonate solution and saturated saline solution. The organic layer was dried over anhydrous magnesium sulfate, filtered and concentrated. The residue was subjected to silica gel column chromatography(eluent: n-hexane/ethylacetate=5/1, v/v) to obtain 0.039 g (Yield 38%) of the title compound as a yellow oil.

$^1$H NMR (CDCl$_3$): δ2.15–2.23(m,1H), 2.79–2.88(m,1H), 3.11–3.15(m,1H), 3.20–3.24(m,1H), 3.66(s,3H), 4.57(d,1H, J=12.09 Hz), 4.81(d,1H, J=12.08 Hz), 5.09(d,1H,J=5.87 Hz), 6.10(bs,1H), 7.17–7.28(m,5H), 7.44 (s,1H), 7.84(s, 1H);

$^{13}$C NMR(CDCl$_3$): δ34.94, 39.67, 46.19, 51.64, 71.27, 99.08, 111.28, 128.21, 128.28, 128.73, 136.80, 137.36, 139.85, 147.71, 152.67, 168.08; ESIMS: 330(M+1).

BIOLOGICAL EXAMPLE 1

Inhibitory Effect on HBV Replication

Test for identifying the anti HBV effect of the compound of the present invention was carried out according to a known assay method (see, Korba and Milman, Antiviral Res., 15, 217, 1991). The assay procedure is briefly described in the following.

A. Cell culture 2.2.15. cell was cultured and preserved in RPM 11640 culture medium containing 5% fetal bovine serum(FBS), 2 mM glutamine and 50 μg/ml gentamicin sulfate. Resistance to G418 of the cell culture and degree of Mycoplasma contamination were examined according to conventional methods.

Cells (1×10$^4$/cm$^2$) were inoculated into a multi-well tissue culture plate, confluently cultured for 7 days, and then kept for 2 or 3 days in confluent condition to stabilize the HBV DNA level. Then, culture medium was replaced 24 hours before cells were exposed to test compound. During the treatment of 9 days, culture medium was replaced and then test compound was added to the fresh culture medium at intervals of 24 hours. Culture medium was collected immediately before the first introduction of test compound, and after 3, 6, 9 days, respectively, and stored at −70° C. before HBV DNA analysis. Then, cytolysis was carried out to analyze the intracellular HBV DNA.

B. Extraction of DNA and RNA

To analyze the extracellular HBV DNA, 0.2 ml of culture medium was incubated in 1M NaOH/10×SSC (1×SSC=0.15M NaCl/0.015M sodium citrate, pH 7.2) for 20 minutes at 25° C. and then immediately applied to a nitrocellulose membrane presoaked in 20×SSC using a slot blot apparatus. The sample was washed twice with 0.5 ml of 1M Tris/2M NaCl (pH 7.2) and once with 0.5 ml of 20×SSC to neutralize, and then it was washed again with 2×SSC and heated at 80° C. for one hour under vacuum. Generally, the cells which have been cultured and preserved in a dish having a diameter of 10 cm are dissolved in 6 ml of lysis buffer, and the extracellular DNA is prepared according to the method of Korba et al., 1991.

C. Electrophoresis in Gel

10 μg/lane of cellular DNA sample was digested with restriction enzyme Hind III. Then, the digested sample was applied to 1% agarose gel electrophoresis and transferred to a nitrocellulose membrane.

D. Hybridization Analysis of HBV DNA 3.2 kb HBV DNA fragment obtained by EcoR 1-digestion and purification was labeled with [$^{32}$P]dCTP using nick translation method. This labeled fragment was used as a hybridization probe. Conditions for hybridization and post-washing were controlled by referring to the method of Korba et al., 1991 and HBV nucleic acid content among test sample was determined by Ambis beta scanner. The relative radioactivity of $^{32}$P hybridized to the test sample was compared with that of $^{32}$P hybridized to the standard amount of HBV DNA which was applied to each nitrocellulose membrane filter (gel or slot blot). From the calibration curve, the amount of HBV DNA corresponding to the relative cpm value was calculated.

Since the content of intracellular and extracellular HBV DNA has some inherent variations, only inhibition greater than 3.5-fold in the case of HBV virion DNA or 3.0-fold in the case of HBV DNA replication intermediates from the average level of HBV DNA formed in the untreated cell were considered to be statistically significant (P<0.05) in the present experiment. The lever of HBV DNA integrated during each cellular DNA preparation (which remains constant per cell in the present experiment) was used to calculate the level of intracellular HBV DNA formed, thereby the technical variations inherent in the blot hybridization analysis can be eliminated. Typical values for extracellular HBV Yirion DNA in the untreated cells ranged from 50 to 150 pg/ml culture medium with an average value of about 75 pg/ml. Intracellular HBV DNA replication intermediates (RI) in the untreated cells ranged from 50 to 100 pg/μg cellular DNA with an average value of about 74 pg/μg. On the basis of the results from the hybridization analysis carried out in the present invention, 1.0 pg of intracellular HBV DNA/μg cellular DNA corresponded to 2 to 3 genome copies per cell, and 1.0 pg of extracellular HBV DNA/ml in culture medium corresponded to 3×10$^5$ virus particles.

According to the method as explained above, the inhibitory effect of the compound of the present invention on HBV replication was evaluated. Herein, untreated group was used as a control and ddC (dideoxy cytidine) known as a potent therapeutic agent for hepatitis as well as AIDS was used as a comparative compound. The anti viral activities of the novel genipin derivative of formula (I) are described in the following Table 2.

BIOLOGICAL EXAMPLE 2

Cytotoxicity Test

Cytotoxicity test was carried out in order to determine whether the anti viral effect of the compound according to the present invention is due to the general influence on cell growth or not. In the present experiment, neutral red dye uptake method was used. This is a standard method widely utilized for examining cell survival, by which the variety of relations between viruses such as HSV or HIV and host organism can be understood.

Cytotoxicity test was performed on a 96-well tissue culture plate. Cells were cultured and treated with test compounds in the same manner as Biological Example 1, and the experiments at 4-kind concentrations were repeated threetimes, respectively. Since the relative toxicity can be determined from the uptake level of neutral red dye, quantitative analysis was carried out using the absorbance of internalized dye at 510 nm ($A_{510}$). The test results on cytotoxicity are also described in the following Table 2.
Table 2.
Inhibitory effect of the compound of formula (I) on HBV replication in 2.2.15 cell culture, cytotoxicity, and SI (Selectivity Index, $IC_{50}/ED_{50}$)

| COMPOUND NO. | $ED_{50}$ ($\mu$M) | $IC_{50}$ ($\mu$M) | SI |
|---|---|---|---|
| 1 | >500 | 120 | — |
| 2 | 30 | 90 | 3.0 |
| 11 | 30 | >200 | >6.7 |
| 13 | 20 | 50 | 2.5 |
| 14 | 15 | 130 | 8.7 |
| ddC | 15 | >30 | >2.0 |

As can be seen from the results of Table 2, the compound of formula (I) according to the present invention exhibits a potent inhibitory activity on HBV replication and its safety has been remarkably improved compared with the known compound ddC. Therefore, it is expected that the compound of the present invention can be preferably used in the treatment of hepatitis B.

What is claimed is:

1. A compound represented by the following formula (I):

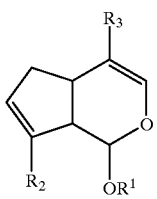

(I)

in which $R_1$ represents lower alkyl, benzyl, or $C_1$–$C_{11}$ alkylcarbonyl which can be substituted with phenyl, phenoxy, pyridyl, t-butyl or thienyl, $R_2$ represents hydroxymethyl, formyl, acetyl, hydroxyiminomethyl, methoxyiminomethyl, lower alkylaminomethyl, acetylthiomethyl, mercaptomethyl, 2,2-dimethyl-1,3-dioxolan-5-ylmethyloxymethyl, 2,3-dihydroxypropyloxymethyl, 6-aminofuran-9-ylmethyl, 4-amino-2-hydroxy-5-methylpyrimidin-1-ylmethyl, 2,4-dihydroxy-5-methylpyrimidin-1-ylmethyl, 5-hydroxymethyl-1,3-oxathiolan-2-yl, or $C_1$–$C_{11}$ alkylcarbonyloxymethyl which can be substituted with phenyl, phenoxy, pyridyl, t-butyl or thienyl, and $R_3$ represents methoxycarbonyl, formyl, hydroxyiminomethyl, methoxyiminomethyl, 4-methoxybenzyloxymethyl or acetyloxymethyl, provided that $R_3$ is not methoxycarbonyl when $R_1$ is lower alkyl, acetyl or t-butylcarbonyl and $R_2$ is hydroxymethyl, formyl, hydroxyiminomethyl, acetyloxymethyl or t-butylcarbonyloxymethyl, and $R_3$ is not acetyloxymethyl when $R_1$ is t-butylcarbonyl and $R_2$ is acetyloxymethyl, its pharmaceutically acceptable salt, or stereoisomer.

2. The compound of claim 1, wherein $R_1$ represents lower alkyl, benzyl, or $C_1$–$C_{11}$ alkylcarbonyl which can be substituted with phenyl, phenoxy, pyridyl, t-butyl or thienyl, $R_2$ represents formyl, hydroxyiminomethyl, or $C_1$–$C_{11}$ alkylcarbonyloxymethyl which can be substituted with phenyl, phenoxy, pyridyl, t-butyl or thienyl, and $R_3$ represents methoxycarbonyl, formyl, or 4-methoxy-benzyloxymethyl.

3. The compound of claim 2, wherein $R_1$ represents $C_1$–$C_{11}$ alkylcarbonyl which can be substituted with phenyl, phenoxy, pyridyl, t-butyl or thienyl, $R_2$ represents formyl or $C_1$–$C_{11}$ alkylcarbonyloxymethyl having the same substituent with $R_1$, and $R_3$ represents methoxycarbonyl.

4. A pharmaceutical composition for the treatment of hepatitis B comprising as an active ingredient the compound of formula (I) defined in claim 1 together with a pharmaceutically acceptable inert carrier.

5. The composition of claim 4, wherein the inert carrier is one or more selected from a group consisting of lactose, starch, mannitol and cottonseed oil.

* * * * *